United States Patent [19]

Israel et al.

[11] 4,299,822

[45] Nov. 10, 1981

[54] N-TRIFLUOROACETYLADRIAMYCIN-14-O-HEMIGLUTARATE AND -HEMIADIPATE AND THERAPEUTIC COMPOSITIONS CONTAINING SAME

[75] Inventors: Mervyn Israel, Needham, Mass.; Gopalakrishnan Potti, Lexington, Ky.

[73] Assignee: Sidney Farber Cancer Institute, Inc., Boston, Mass.

[21] Appl. No.: 157,861

[22] Filed: Jun. 9, 1980

[51] Int. Cl.$^3$ .................. C07H 15/24; A61K 31/71
[52] U.S. Cl. ................................ 424/180; 536/17 A
[58] Field of Search ...................... 536/17 A; 424/180

[56] References Cited

U.S. PATENT DOCUMENTS 4,035,566 7/1977 Israel et al. .................. 536/17 A
4,166,848 9/1979 Bernardi et al. .............. 536/17 A

FOREIGN PATENT DOCUMENTS 2135221 12/1972 France .......................... 536/17 A
1368680 10/1974 United Kingdom ......... 536/17 A Primary Examiner—Johnnie R. Brown

[57] ABSTRACT

N-Trifluoroacetyladriamycin-14-O-hemiglutarate and -hemiadipate having antitumor activity and low toxicity are soluble in water at a physiological pH ranging from 7.2 to 7.5.

6 Claims, No Drawings

N-TRIFLUOROACETYLADRIAMYCIN-14-O-HEMIGLUTARATE AND -HEMIADIPATE AND THERAPEUTIC COMPOSITIONS CONTAINING SAME

The invention described herein was made in the course of work under a grant or award from the Department of Health, Education and Welfare.

This invention relates to certain novel water-soluble chemical compounds having antitumor activity against murine P388 and LI210 leukemias together with low toxicity; and to therapeutic compositions containing these compounds together with a pharmaceutically acceptable non-toxic aqueous carrier which are useful for administration to mice having certain tumors for extending their life spans.

Adriamycin[1] and daunomycin[2] and related compounds such as certain N-trifluoroacetyl derivatives have been described in U.S. Pat. Nos. 3,590,028 and 3,803,124. The latter patent also describes the preparation of N-trifluoroacetyladriamycin-14-acetate (identified by the name 14-acetoxy-N-trifluoroacetyldaunomycin) but does not indicate that this compound possesses any therapeutic or pharmacological activity and suggests no utility for it except its use in preparing N-trifluoroacetyladriamycin, from which adriamycin may be chemically derived.

[1]Also known as doxorubicin.
[2]Also known as daunorubicin.

Adriamycin differs from daunomycin in that the former contains a hydroxyl group in the 14-position while the latter does not, having hydrogen instead. The structural formula of adriamycin is as follows:

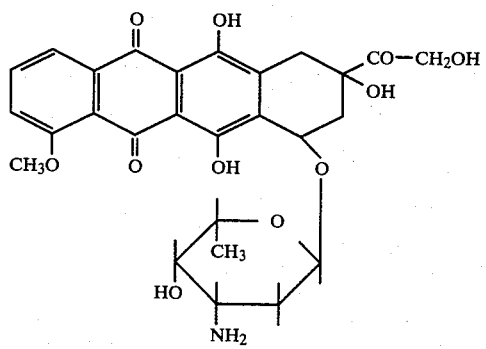

In U.S. Pat. No. 4,035,566 there have been described N-trifluoroacetyladriamycin-14-alkanoates in which the alkanoate has from 2 to 10 carbon atoms, and also therapeutic compositions containing such compounds; the compounds are described as having antitumor activity.

Although daunorubicin and adriamycin are of importance in the clinical management of a spectrum of neoplastic diseases, including leukemias, lymphomas, and various solid tumors, especially soft-tissue sarcomas, their use is compromised by toxic side-effects, especially acute myelosuppression and cumulative dose-related cardiac toxicity, both of which are dose-limiting. N-Trifluoroacetyladriamycin-14-valerate, one of the compounds described in U.S. Pat. No. 4,035,566, has been extensively tested and has been found to be therapeutically superior to adriamycin and to daunomycin. In addition, it is less toxic in general, and in particular significantly less cardiotoxic than the parent drug both in animals and in human clinical tests.

However, this compound is highly lipophilic and, therefore, is essentially water-insoluble. For clinical use the drug must be formulated for intravenous administration in a surfactant-containing vehicle. The formulation currently in use involves the compound dissolved at a final concentration of 0.35 mg/ml in 0.5% Emulphor EL-620 (polyethoxylated castor oil)-0.5% ethanol-99% saline. Thus, a patient with a body surface area of 1.0 $m^2$ receiving a 600 $mg/m^2$ dose of the drug, the usual clinical dose administered over a 24 hour period once every 21 days, must take in about 1.7 liters of infusate. These large volumes dictate that they be given as a 24-hour continuous infusion. Some patients at 400 $mg/m^2$ have experienced, about two-thirds through the infusion, an apparent vehicle-associated chest pain syndrome. Administration of steroid (hydrocortisone hemisuccinate) eliminated the symptom complex in those cases, and routine steroid prophylaxis has been introduced; this procedure has prevented the chest pain symptomology with all subsequent courses of drug.

It has now been found that N-trifluoroacetyladriamycin-14-O-hemiglutarate and -hemiadipate display a cytotoxicity or anti-tumor activity greater than that of adriamycin and approximately equal to that of N-trifluoroacetyladriamycin-14-valerate, and are significantly less toxic to mice than adriamycin or daunomycin in terms of pharmacological properties; at the same time they exhibit solubility in water at physiological pH in the range pH 7.2–7.5 many times greater than that of N-trifluoroacetyladriamycin-14-valerate under the same conditions and are soluble even in the absence of dispersing agents and of alcohol. Moreover, despite the much higher water solubility, the hemiglutarate and hemiadipate of the present invention display excellent resistance to hydrolysis and are consequently sufficiently stable to be useful in the form of aqueous solutions subject to shipment and storage over substantial periods of time.

Consequently, the compounds of the present invention can be administered in the same vehicle as currently employed clinically for the valerate analog but at much higher concentrations so that a single bolus dose of 10 to 20 ml. can replace the 24-hour infusion procedure.

The novel compounds of the present invention can be prepared by procedures analogous to those employed for making N-trifluoroacetyladriamycin-14-alkanoates as described in U.S. Pat. No. 4,035,566 by substituting, in general, glutaric or adipic acid monosodium salt, as the case may be, for alkanoic acid sodium salt, as well as by other procedures.

The therapeutic compositions of the present invention containing the novel compounds of the present invention as the active agents can be prepared by dispersing or dissolving the active agent in any pharmaceutically acceptable non-toxic carrier suitable for the desired mode of administration, which may be parenteral, that is, by injection which is intravenous, intramuscular, intraperitoneal, or other conventional mode. Preferably the carrier is an aqueous medium buffered to pH 7.2–7.5, the physiologic range. Any suitable conventional buffer can be used such as Tris, phosphates, bicarbonates or citrates. If desired, saline solution can be used, with pH adjustment and buffering. Nonionic emulsifying agents such as polyethoxylated castor oil, polyethoxylated sorbitan monooleate, or the like, can be present in amounts up to 10% by weight, as well as ethanol, to enhance the solubility of the novel compounds, as in clinical administration of the valerate, but this is generally unnecessary since the compounds are soluble to the extent of approximately 60 mg/ml in water buffered to pH 7.2-7.5 without the addition of emulsifiers or alcohol.

The toxicity and therapeutic effectiveness of the new compounds and active agents of the present invention are shown by in vitro assays and by in vivo evaluations in mice. The in vitro assays measure the growth inhibiting activity of the materials against the CCRF-CEM cell line in culture. The cell line was derived from the peripheral blood of a child with lymphoblastic leukemia as described by Foley et al., Cancer, Volume 18, page 522 et seq. (1965), and the assays were carried out by the procedure of Foley and Lazarus, Biochem. Pharmacol., Volume 16, pages 659 et seq. (1967), the results being reported in terms of the dose in micromoles per liter required to inhibit growth of the cultures by 50% relative to control cultures to which no drug had been added ($ID_{50}$). The in vivo evaluations were made by preparing a 0.2 to 0.7% by weight solution of the active agent in a formulation consisting of 10% by volume of each polyethoxylated castor oil and ethanol in saline and injecting the dosage intraperitoneally. The evaluations were made of the antitumor activity against the murine P388 and murine L1210 leukemias in $BDF_1$ male mice according to standard National Cancer Institute protocols as set forth by Geran et al., Cancer Chemotherap. Rep., Part 3, Volume 3, pages 1 et seq. (1972), except that a qd 1-4 schedule was used in place of qd 1-9 in order to conserve materials.

Optimal dosage was determined by testing doses which were at several multiples of 10 milligrams/kilogram of body weight. Some effectiveness can be observed at dosages ranging from 30 to 70 milligrams/kilogram of body weight, depending upon the particular compound employed.

The following examples are intended to illustrate more fully the preparation of the compounds and their effectiveness without acting as a limitation upon the scope of the invention.

EXAMPLE 1

N-Trifluoroacetyladriamycin-14-O-hemiglutarate

Method 1: Refluxing acetone. A mixture of 14-iodo-N-trifluoroacetyldaunomycin (200 mg, 0.26 mmol) and glutaric acid monosodium salt (1.2 g) was taken in 3 ml of water and then was diluted with 350 ml acetone. The reaction mixture was heated at reflux for 10 hours. After cooling, the reaction mixture was filtered and the filter cake was washed with hot acetone until the washings were no longer colored. The combined filtrate and washings were evaporated to dryness under reduced pressure and the residue was redissolved in chloroform (200 ml). The chloroform solution was washed three times with 150 ml portions of water, dried over anhydrous sodium sulfate, filtered and evaporated to about 2-3 ml volume. This concentrate was chromatographed on a column of silicic acid using chloroform, followed by 0.5% MeOH in chloroform as eluant. A concentrated chloroform solution of the eluted product was triturated with petroleum ether to give 152 mg (76% yield) of product, m.p. 141°-144° C. (dec); $[\alpha]_D +228$ (c=0.046, $CH_3OH$);

UV/VIS $\lambda_{max}^{CH3OH}$ nm (ξ) 233 (29,700), 240 (24,800), 277 (9,900), 478 (8,540), 495 (8,350), 531 (4,270); IR (KBr) $cm^{-1}$ 3450 broad

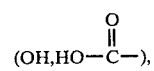

1715, 1705, 1602, 1580 (C=O and quinone). Anal. Calcd. for $C_{34}H_{34}F_3NO_{15}$: C, 54.20; H, 4.56; F, 7.56; N, 1.86. Found: C, 54.06; H, 4.65; F, 7.37; N, 1.86.

The product was also obtained (60% yield) when 14-bromo-N-trifluoroacetyldaunomycin was used in place of the iodo compound as starting material.

Method 2: In ethylene glycol. A mixture of glutaric acid monosodium salt (100 mg) and ethylene glycol (10 ml) was heated to 65°-70° in an oil bath. To this mixture was added 14-iodo-N-trifluoroacetyldaunomycin (50 mg, 0.066 mmole) and the resulting solution was maintained with vigorous stirring at 65°-70° for 1 hour. The reaction mixture was then poured into ice water and the product was extracted into chloroform (3×50 ml). The chloroform solution was washed with water (3×100 ml), dried over anhydrous sodium sulfate for 2 hours, and reduced to a small volume under vacuum. Addition of petroleum ether precipitated a red solid which was separated by filtration, washed with petroleum ether, and dried. The product (45 mg, 90% yield) was further purified by crystallization from chloroform-ethyl ether-petroleum ether to give material identical in all spectral and chromatographic properties with product obtained according to Method 1 above.

Method 3: In dimethyl formamide (DMF). Glutaric acid monosodium salt (40 mg) was dissolved in 10 ml of DMF by heating at 120° for 10 minutes. The solution was cooled to 70° and 14-iodo-N-trifluoroacetyldaunomycin (25 mg, 0.033 mmole) was added with stirring. The reaction mixture was maintained at 65°-70° for 1 hr, cooled, and the DMF removed under vacuum. Isolated and purification, as in Method 2 above, afforded 23 mg of the hemiglutarate product (92% yield).

EXAMPLE 2

N-Trifluoroacetyladriamycin-14-O-hemiadipate

Method 1: Refluxing acetone. A mixture of 14-iodo-N-trifluoroacetyldaunomycin (150 mg, 0.2 mmol) and 1.0 g of adipic acid monosodium salt was taken in 300 ml of acetone containing 2 ml of water. The reaction mixture was heated at reflux for 12 hours. Similar work-up as for the hemiglutarate, Method 1, gave 133 mg (85% yield) of red solid, m.p. 135°-140° (dec.); $[\alpha]+201$ (c=0.016, $CH_3OH$); IR (KBr) $cm^{-1}$ 3460 broad

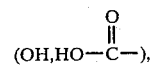

1720, 1710, 1680, 1650, (C=O and quinone);

UV/VIS $\lambda_{max}^{CH3OH}$ nm (ξ) 223 (33,200), 241 (23,800), 276 (9,020), 478 (9,780), 497 (9,590), 532 (4,990).

Anal. Calcd. for $C_{35}H_{36}F_3NO_{15}$: C, 54.76; H, 4.72; F, 7.46; N, 1,82 Found: C, 54.59; H, 4.59; F, 7.22; N, 1.77.

When 14-bromo-N-trifluoroacetyldaunomycin was substituted for the iodo starting material, the hemiadipate was obtained in 64% yield.

Method 2: In ethylene glycol. Treatment of adipic acid monosodium salt (100 mg) and 14-iodo-N-trifluoroacetyldaunomycin (40 mg, 0.053 mmole) in 15 ml ethylene glycol according to the reaction conditions and work-up procedure for the hemiglutarate, Method 2, afforded 38 mg (93% yield) of hemiadipate product identical with material obtained by Method 1, above, in all chemical and physical characteristics.

Method 3: In dimethyl formamide. Reaction of adipic acid monosodium salt (200 mg) and 14-iodo-N-trifluoroacetyldaunomycin (200 mg, 0.26 mmole) in DMF, as for the hemiglutarate, Method 3, afforded 182 mg of hemiadipate product (89% yield).

The solubility in water (buffered at pH 7.40 with Fisher certified monobasic potassium phosphate and sodium hydroxide) of N-trifluoroacetyladriamycin-14-O-hemiglutarate at 22° C. is 65 mg/ml, that of the -hemiadipate is 60 mg/ml, while that of the -valerate is a few micrograms. Stability of the -hemiglutarate and -hemiadipate was measured by dissolving known quantities of each in aqueous buffers at selected pH values. Specimens of each solution were stored 24 hours in the dark at 4° C. and 27° C. respectively, then applied to glass-backed silica gel G TLC plates (250μ thick layer) and the plates were developed in a solvent mixture of chloroform-methanol (95:5 by volume) and spots were visualized by fluorescence under 350 nm light. The amount of hydrolytic product, N-trifluoroacetyladriamycin ($R_f$ 0.58), was quantified by reference to an authentic standard run simultaneously. The results were as follows:

TABLE I

| | | | Percent hydrolyzed | |
|---|---|---|---|---|
| | | $R_f$ | 4° | 27° |
| N-trifluoroacetyladriamycin-14-O-hemiglutarate | pH 7.40 | 0.26 | 0 | 1 |
| | pH 9.00 | | <0.5 | 3 |
| hemiadipate | pH 7.40 | 0.31 | 0 | 0.5 |
| | pH 8.00 | | 0.3 | 1 |
| | pH 9.00 | | 0.5 | 2 |

The following table summarizes the inhibitory activity against CCRF-CEM cells of the compounds of the present invention as well as other materials when tested in vitro as described above.

TABLE II

| Compound | $ID_{50}$ μM |
|---|---|
| Adriamycin | 0.05 |
| N-trifluoroacetyladriamycin-14- | |
| valerate | 0.24 |
| hemiglutarate | 0.28 |
| hemiadipate | 0.31 |

The following table summarizes the in vivo antitumor activity of the same compounds as those in Table I, evaluated against murine P388 leukemia as described above. All compounds were administered intraperitoneally, adriamycin in clinical formulation (1 part adriamycin plus 5 parts lactose, in 0.9% saline), the other compounds in 10% Emulphor EL-620, 10% ethanol, 80% isotonic saline.

TABLE III

| | each dose, mg/kg body wt. | Survival | | | |
|---|---|---|---|---|---|
| | | Median day of death (range) | % ILS+ | No. alive on d 30 | on d 60 |
| Compound | | | | | |
| Zero dose controls | — | 11.0 (10–14) | | 0/22 | |
| Adriamycin | 1.0 | 20.0 (18–27) | 81 | 0/7 | |
| | 2.0 | 21.0 (20–32) | 90 | 2/7 | 1/7 |
| | 3.0 | 31.0 (23–36) | 181 | 4/7 | 2/7 |
| | 4.0 | 18.0 (7–28) | 63 | 0/7 | |
| | 5.0 | 9.0 (7–27) | −19 | 0/7 | |
| N-trifluoroacetyladriamycin-14- | | | | | |
| -valerate | 20.0 | 42.0 (21–42) | 281 | 5/7 | 3/7 |
| | 30.0 | (21–26) | | 4/7 | 4/7 |
| | 40.0 | (30,71) | | 6/7 | 6/7 |
| | 50.0 | 95.0 (24–95) | 763 | 5/7 | 5/7 |
| | 60.0 | 90.0 (9–90) | 718 | 5/7 | 5/7 |
| -hemiglutarate | 30.0 | 20.0 (20–35) | 81 | 2/7 | 0/7 |
| | 40.0 | 23.0 (20–35) | 109 | 2/7 | 1/7 |
| | 50.0 | 30.0 (20–42) | 172 | 3/7 | 2/7 |
| | 60.0 | (20,29) | | 5/7 | 4/7 |
| | 70.0 | (25–36) | | 5/7 | 4/7 |
| -hemiadipate | 40.0 | (25) | | 6/7 | 6/7 |
| | 50.0 | (23,45) | | 6/7 | 5/7 |
| | 60.0 | (24,93) | | 6/7 | 6/7 |
| | 70.0 | (61–77) | | 7/7 | 7/7 |

+Percent increase in life span relative to untreated controls

In addition, tests of N-trifluoroacetyladriamycin-14-hemiadipate show it to be highly effective in prolonging the survival of mice bearing the L1210 leukemia, as shown by the results set forth in the following table. All compounds were administered intraperitoneally; in tests (1) and (2), the compounds were in 10% Emulphor EL-620, 10% ethanol, and 80% isotonic saline. In test (3) the compound was in aqueous buffer containing monobasic potassium phosphate and sodium hydroxide (0.05 M), pH 7.40:

TABLE IV

| | Compound | Optimal Dose mg/kg/d × 4▲ | Median Survival, day | % ILS* | No. alive on d 50 |
|---|---|---|---|---|---|
| | Zero-dose control | | 9.0 | | 0/15ξ |
| (1) | N-Trifluoroacetyladriamycin-14-valerate | 50.0 | | >456 | 5/7 |
| | | 60.0 | | >456 | 6/7 |
| (2) | N-Trifluoroacetyladriamycin-14-hemiadipate | 50.0 | | >456 | 7/7 |
| | | 60.0 | | >456 | 6/7 |
| (3) | Same as (2) | 50.0 | | >456 | 5/7 |
| | | 60.0 | | >456 | 7/7 |

▲Treatment ip once daily on days 1,2,3 and 4.
*Percent median increase in life span relative to untreated controls, calculated as of day 50.
ξAll animals dead between day 8 and 11

What is claimed is:
1. N-Trifluoroacetyladriamycin-14-O-hemiglutarate.
2. N-Trifluoroacetyladriamycin-14-O-hemiadipate.
3. A therapeutic composition exhibiting antitumor activity against murine P388 and murine L1210 leukemias in mice, said composition consisting essentially of a pharmaceutically acceptable non-toxic carrier and an effective amount of a compound as claimed in claim 1.
4. A therapeutic composition as claimed in claim 3 in which said carrier is water buffered at pH 7.2–7.5.
5. A therapeutic composition exhibiting antitumor activity against murine P388 and murine L1210 leukemias in mice, said composition consisting essentially of a pharmaceutically acceptable non-toxic carrier and an effective amount of a compound as claimed in claim 2.
6. A therapeutic composition as claimed in claim 5 in which said carrier is water buffered at pH 7.2–7.5.

* * * * *

UNITED STATES PATENT AND TRADEMARK OFFICE
CERTIFICATE OF CORRECTION

PATENT NO. : 4,299,822
DATED : November 10, 1981
INVENTOR(S) : Mervyn Israel et al.

It is certified that error appears in the above-identified patent and that said Letters Patent are hereby corrected as shown below:

Column 4, line 9, "1602" should be --1620--.

Signed and Sealed this

Ninth Day of February 1982

[SEAL]

Attest:

GERALD J. MOSSINGHOFF

Attesting Officer          Commissioner of Patents and Trademarks